US009812114B2

(12) United States Patent
Alderson et al.

(10) Patent No.: US 9,812,114 B2
(45) Date of Patent: Nov. 7, 2017

(54) SYSTEMS AND METHODS FOR CONTROLLING ADAPTIVE NOISE CONTROL GAIN

(71) Applicant: Cirrus Logic International Semiconductor Ltd., Edinburgh (GB)

(72) Inventors: Jeffrey D. Alderson, Austin, TX (US); Jon D. Hendrix, Wimberley, TX (US); Sang-Ik Terry Cho, Austin, TX (US); Chin Huang Yong, Austin, TX (US); John L. Melanson, Austin, TX (US)

(73) Assignee: Cirrus Logic, Inc., Austin, TX (US)

( * ) Notice: Subject to any disclaimer, the term of this patent is extended or adjusted under 35 U.S.C. 154(b) by 79 days.

(21) Appl. No.: 15/058,866

(22) Filed: Mar. 2, 2016

(65) Prior Publication Data

US 2017/0256248 A1 Sep. 7, 2017

(51) Int. Cl.

*A61F 11/06* (2006.01)
*G10K 11/16* (2006.01)
*G10K 11/178* (2006.01)

(52) U.S. Cl.

CPC ........ *G10K 11/178* (2013.01); *G10K 11/1784* (2013.01); *G10K 11/1786* (2013.01);

(Continued)

(58) Field of Classification Search

CPC G10K 11/175; G10K 11/178–11/1788; G10K 11/00; G10K 11/30; G10K 11/301;

(Continued)

(56) References Cited

U.S. PATENT DOCUMENTS 5,278,913 A 1/1994 Delfosse et al.
5,633,795 A * 5/1997 Popovich ........... G10K 11/1786 381/71.11

(Continued)

FOREIGN PATENT DOCUMENTS

EP 2395501 A1 12/2011
WO 2012166272 A2 12/2012

OTHER PUBLICATIONS

Combined Search and Examination Report under Sections 17 and 18(3), United Kingdom Application No. GB1606528.6, dated Oct. 19, 2016.

(Continued)

*Primary Examiner* — Xu Mei
(74) *Attorney, Agent, or Firm* — Jackson Walker L.L.P.

(57) ABSTRACT

A method may include adaptively generating an anti-noise signal for countering the effects of ambient audio sounds at an acoustic output of the transducer by adapting a response of an adaptive filter that filters a reference microphone signal in conformity with an error microphone signal and the reference microphone signal to minimize the ambient audio sounds in the error microphone, generating a scaled anti-noise signal by applying a scaling factor to the anti-noise signal, further adjusting the response of the adaptive filter independent of a source audio signal by altering an input to the coefficient control block of the adaptive filter to compensate for the scaling factor, and combining the scaled anti-noise signal with the source audio signal to generate an audio signal provided to the transducer.

34 Claims, 5 Drawing Sheets

(52) U.S. Cl.
CPC ................ *G10K 2210/1081* (2013.01); *G10K 2210/3014* (2013.01); *G10K 2210/3028* (2013.01); *G10K 2210/3056* (2013.01)

(58) Field of Classification Search
CPC ........... G10K 11/1081; G10K 11/3014; G10K 11/3022; G10K 11/3023; G10K 11/30232; G10K 11/3027; G10K 11/3028; G10K 11/3045; G10K 11/3046; G10K 11/3056
USPC .... 381/71.11, 71.1, 71.8, 71.9, 71.12, 71.13, 381/71.14, 72, 73.1, 94.1–94.8
See application file for complete search history.

(56) References Cited

U.S. PATENT DOCUMENTS

| | | | | |
|---|---|---|---|---|
| 6,275,592 | B1 * | 8/2001 | Vartiainen ............ | G10K 11/178<br>381/71.11 |
| 6,907,128 | B2 * | 6/2005 | Kimura .................. | G01G 3/147<br>381/71.1 |
| 8,824,695 | B2 * | 9/2014 | Bakalos ............. | G10K 11/1788<br>381/71.8 |
| 8,948,407 | B2 * | 2/2015 | Alderson ........... | G10K 11/1784<br>379/406.12 |
| 9,368,099 | B2 * | 6/2016 | Alderson ........... | G10K 11/1784 |
| 9,460,701 | B2 * | 10/2016 | Yong ...................... | G10K 11/16 |
| 9,462,376 | B2 * | 10/2016 | Alderson ............... | H04R 3/002 |
| 9,666,176 | B2 * | 5/2017 | Milani ............... | G10K 11/1788 |
| 2008/0181422 | A1 * | 7/2008 | Christoph .......... | G10K 11/1784<br>381/73.1 |
| 2008/0310646 | A1 * | 12/2008 | Amada ................. | G10L 19/008<br>381/73.1 |
| 2013/0259250 | A1 | 10/2013 | Nicholson et al. | |
| 2014/0086425 | A1 | 3/2014 | Jensen et al. | |
| 2014/0314244 | A1 | 10/2014 | Yong et al. | |
| 2015/0189432 | A1 * | 7/2015 | Yuzuriha .................. | H04R 3/00<br>381/94.1 |

OTHER PUBLICATIONS

Kuo, Sen M., and Morgan, Dennis, R., Active Noise Control: A Tutorial Review, Proceedings of the IEEE, vol. 87, No. 6, Jun. 1999, pp. 943-973.

International Search Report and Written Opinion of the International Searching Authority, International Application No. PCT/US2017/020149, dated May 19, 2017.

* cited by examiner

SYSTEMS AND METHODS FOR CONTROLLING ADAPTIVE NOISE CONTROL GAIN

FIELD OF DISCLOSURE

The present disclosure relates in general to adaptive noise cancellation in connection with an acoustic transducer, and more particularly, to detection and cancellation of ambient noise present in the vicinity of the acoustic transducer, including allowing for control of a level of anti-noise generated by adaptive noise cancellation.

BACKGROUND

Wireless telephones, such as mobile/cellular telephones, cordless telephones, and other consumer audio devices, such as mp3 players, are in widespread use. Performance of such devices with respect to intelligibility can be improved by providing noise canceling using a microphone to measure ambient acoustic events and then using signal processing to insert an anti-noise signal into the output of the device to cancel the ambient acoustic events. Because the acoustic environment around personal audio devices, such as wireless telephones, can change dramatically, depending on the sources of noise that are present and the position of the device itself, it is desirable to adapt the noise canceling to take into account such environmental changes.

However, an audio device that provides active noise cancellation (ANC) to a listener may provide more ANC effect than the listener desires. Thus, a listener may wish to selectively reduce the amount of ANC. In a noise cancellation system with a fixed feedback filter or a fixed feedforward filter for generating anti-noise, reducing the ANC effect may be easily accomplished by reducing the gain of the anti-noise in the fixed feedback filter, the fixed feedforward filter, or both. On the other hand, in an adaptive system, simply reducing gain of an anti-noise path (whether in the fixed feedback filter, the feedforward filter, or both) may not serve to reduce the ANC effect, as the adaptive system may adapt further to compensate (e.g., undo) the reduction of anti-noise gain. As a result, the ANC effect would return to what it was before the listener reduced the gain. Accordingly, using traditional approaches, a listener has no effective means to reduce ANC effect in an adaptive system.

SUMMARY

In accordance with the teachings of the present disclosure, the disadvantages and problems associated with existing approaches to adaptive noise cancellation may be reduced or eliminated.

In accordance with embodiments of the present disclosure, an integrated circuit for implementing at least a portion of a personal audio device may include an output, a reference microphone input, an error microphone input, and a processing circuit. The output may provide a signal to a transducer including both a source audio signal for playback to a listener and a scaled anti-noise signal for countering the effect of ambient audio sounds in an acoustic output of the transducer. The reference microphone input may receive a reference microphone signal indicative of the ambient audio sounds. The error microphone input may receive an error microphone signal indicative of the output of the transducer and the ambient audio sounds at the transducer. The processing circuit may include an adaptive filter having a response that generates an unscaled anti-noise signal from the reference microphone signal to reduce the presence of the ambient audio sounds heard by the listener, a scaling portion that generates the scaled anti-noise signal by applying a scaling factor to the anti-noise signal, a coefficient control block that shapes the response of the adaptive filter in conformity with the reference microphone signal and the error microphone signal by adapting the response of the adaptive filter to minimize the ambient audio sounds at the error microphone signal, and a biasing portion configured to further adjust the response of the adaptive filter independent of the source audio signal by altering an input to the coefficient control block of the adaptive filter to compensate for the scaling factor.

In accordance with these and other embodiments of the present disclosure, a method may include receiving a reference microphone signal indicative of the ambient audio sounds, receiving an error microphone signal indicative of the output of the transducer and the ambient audio sounds at the transducer, generating a source audio signal for playback to a listener, adaptively generating an anti-noise signal for countering the effects of ambient audio sounds at an acoustic output of the transducer by adapting a response of an adaptive filter that filters the reference microphone signal in conformity with the error microphone signal and the reference microphone signal to minimize the ambient audio sounds in the error microphone, generating a scaled anti-noise signal by applying a scaling factor to the anti-noise signal, further adjusting the response of the adaptive filter independent of the source audio signal by altering an input to the coefficient control block of the adaptive filter to compensate for the scaling factor, and combining the scaled anti-noise signal with the source audio signal to generate an audio signal provided to the transducer.

Technical advantages of the present disclosure may be readily apparent to one skilled in the art from the figures, description and claims included herein. The objects and advantages of the embodiments will be realized and achieved at least by the elements, features, and combinations particularly pointed out in the claims.

It is to be understood that both the foregoing general description and the following detailed description are examples and explanatory and are not restrictive of the claims set forth in this disclosure.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION

The present disclosure encompasses noise canceling techniques and circuits that can be implemented in a personal audio device, such as a wireless telephone. The personal audio device includes an ANC circuit that may measure the ambient acoustic environment and generate a signal that is injected in the speaker (or other transducer) output to cancel ambient acoustic events. A reference microphone may be provided to measure the ambient acoustic environment and an error microphone may be included for controlling the adaptation of the anti-noise signal to cancel the ambient audio sounds and for correcting for the electro-acoustic path from the output of the processing circuit through the transducer.

Figure 1A:
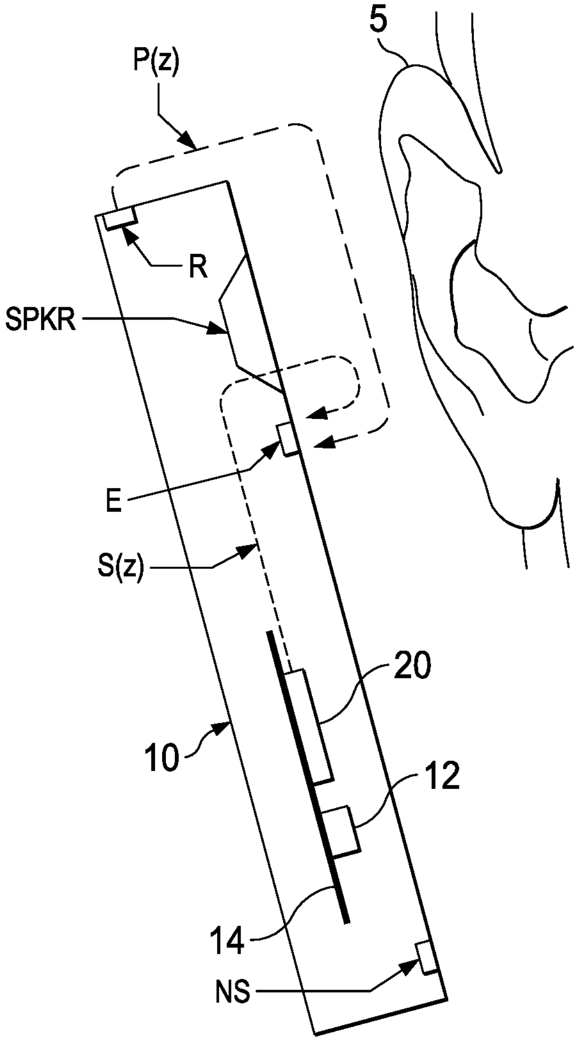
FIG. 1A is an illustration of an example wireless telephone, in accordance with embodiments of the present disclosure.

Referring now to FIG. 1A, a wireless telephone 10 as illustrated in accordance with embodiments of the present disclosure is shown in proximity to a human ear 5. Wireless telephone 10 is an example of a device in which techniques in accordance with embodiments of this disclosure may be employed, but it is understood that not all of the elements or configurations embodied in illustrated wireless telephone 10, or in the circuits depicted in subsequent illustrations, are required in order to practice the inventions recited in the claims. Wireless telephone 10 may include a transducer such as speaker SPKR that reproduces distant speech received by wireless telephone 10, along with other local audio events such as ringtones, stored audio program material, injection of near-end speech (i.e., the speech of the user of wireless telephone 10) to provide a balanced conversational perception, and other audio that requires reproduction by wireless telephone 10, such as sources from webpages or other network communications received by wireless telephone 10 and audio indications such as a low battery indication and other system event notifications. A near-speech microphone NS may be provided to capture near-end speech, which is transmitted from wireless telephone 10 to the other conversation participant(s).

Wireless telephone 10 may include ANC circuits and features that inject an anti-noise signal into speaker SPKR to improve intelligibility of the distant speech and other audio reproduced by speaker SPKR. A reference microphone R may be provided for measuring the ambient acoustic environment, and may be positioned away from the typical position of a user's mouth, so that the near-end speech may be minimized in the signal produced by reference microphone R. Another microphone, error microphone E, may be provided in order to further improve the ANC operation by providing a measure of the ambient audio combined with the audio reproduced by speaker SPKR close to ear 5, when wireless telephone 10 is in close proximity to ear 5. In other embodiments, additional reference and/or error microphones may be employed. Circuit 14 within wireless telephone 10 may include an audio CODEC integrated circuit (IC) 20 that receives the signals from reference microphone R, near-speech microphone NS, and error microphone E and interfaces with other integrated circuits such as a radio-frequency (RF) integrated circuit 12 having a wireless telephone transceiver. In some embodiments of the disclosure, the circuits and techniques disclosed herein may be incorporated in a single integrated circuit that includes control circuits and other functionality for implementing the entirety of the personal audio device, such as an MP3 player-on-a-chip integrated circuit. In these and other embodiments, the circuits and techniques disclosed herein may be implemented partially or fully in software and/or firmware embodied in computer-readable media and executable by a controller or other processing device.

In general, ANC techniques of the present disclosure measure ambient acoustic events (as opposed to the output of speaker SPKR and/or the near-end speech) impinging on reference microphone R, and by also measuring the same ambient acoustic events impinging on error microphone E, ANC processing circuits of wireless telephone 10 adapt an anti-noise signal generated from the output of reference microphone R to have a characteristic that minimizes the amplitude of the ambient acoustic events at error microphone E. Because acoustic path P(z) extends from reference microphone R to error microphone E, ANC circuits are effectively estimating acoustic path P(z) while removing effects of an electro-acoustic path S(z) that represents the response of the audio output circuits of CODEC IC 20 and the acoustic/electric transfer function of speaker SPKR including the coupling between speaker SPKR and error microphone E in the particular acoustic environment, which may be affected by the proximity and structure of ear 5 and other physical objects and human head structures that may be in proximity to wireless telephone 10, when wireless telephone 10 is not firmly pressed to ear 5. While the illustrated wireless telephone 10 includes a two-microphone ANC system with a third near-speech microphone NS, some aspects of the present invention may be practiced in a system that does not include separate error and reference microphones, or a wireless telephone that uses near-speech microphone NS to perform the function of the reference microphone R. Also, in personal audio devices designed only for audio playback, near-speech microphone NS will generally not be included, and the near-speech signal paths in the circuits described in further detail below may be omitted, without changing the scope of the disclosure, other than to limit the options provided for input to the microphone covering detection schemes.

Figure 1B:
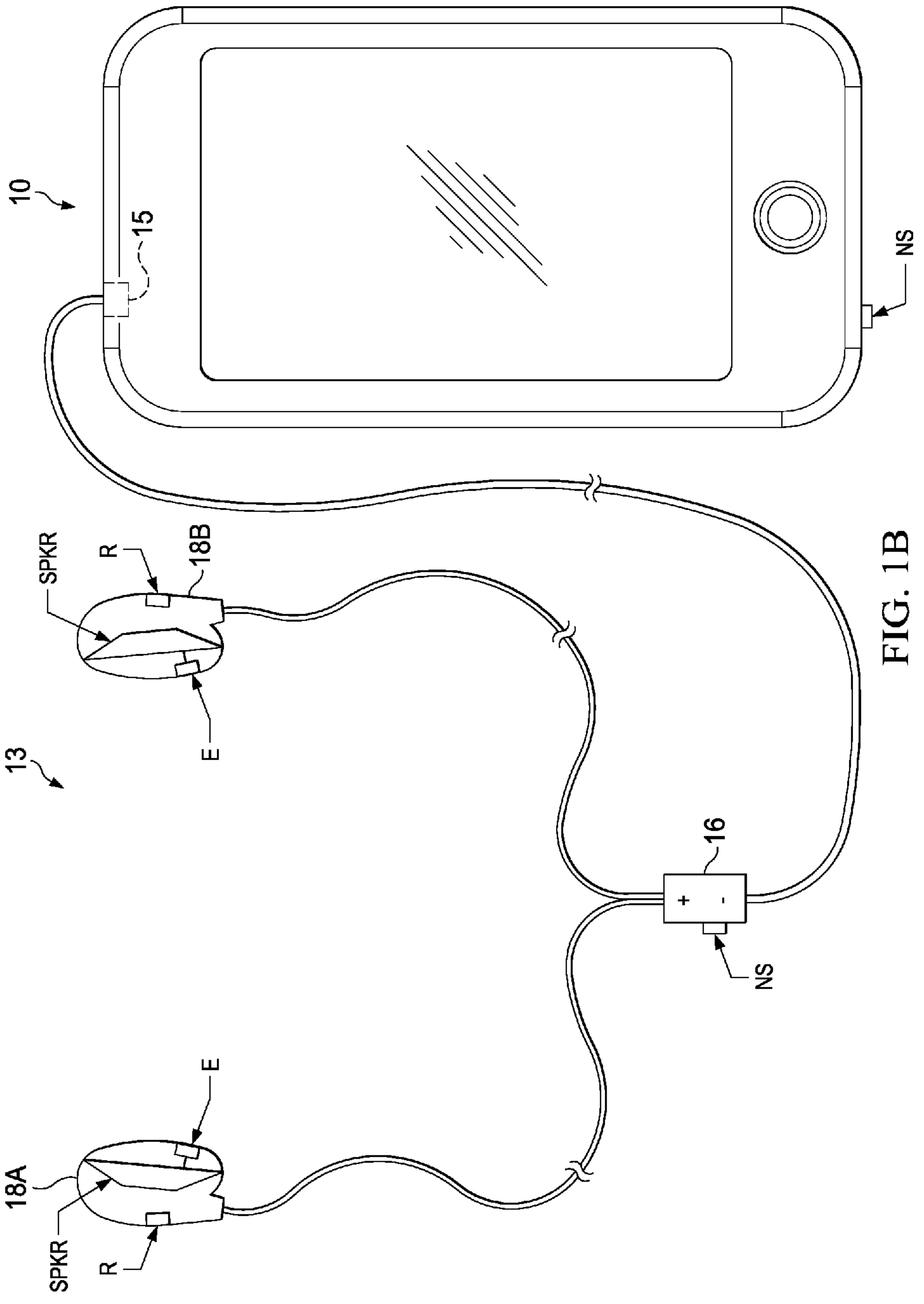
FIG. 1B is an illustration of an example wireless telephone with a headphone assembly coupled thereto, in accordance with embodiments of the present disclosure.

Referring now to FIG. 1B, wireless telephone 10 is depicted having a headphone assembly 13 coupled to it via audio port 15. Audio port 15 may be communicatively coupled to RF integrated circuit 12 and/or CODEC IC 20, thus permitting communication between components of headphone assembly 13 and one or more of RF integrated circuit 12 and/or CODEC IC 20. As shown in FIG. 1B, headphone assembly 13 may include a combox 16, a left headphone 18A, and a right headphone 18B. As used in this disclosure, the term "headphone" broadly includes any loudspeaker and structure associated therewith that is intended to be mechanically held in place proximate to a listener's ear canal, and includes without limitation earphones, earbuds, and other similar devices. As more specific examples, "headphone" may refer to intra-concha earphones, supra-concha earphones, and supra-aural earphones.

Combox 16 or another portion of headphone assembly 13 may have a near-speech microphone NS to capture near-end speech in addition to or in lieu of near-speech microphone NS of wireless telephone 10. In addition, each headphone 18A, 18B may include a transducer such as speaker SPKR that reproduces distant speech received by wireless telephone 10, along with other local audio events such as ringtones, stored audio program material, injection of near-end speech (i.e., the speech of the user of wireless telephone 10) to provide a balanced conversational perception, and other audio that requires reproduction by wireless telephone 10, such as sources from webpages or other network communications received by wireless telephone 10 and audio indications such as a low battery indication and other system event notifications. Each headphone 18A, 18B may include a reference microphone R for measuring the ambient acoustic environment and an error microphone E for measuring of the ambient audio combined with the audio reproduced by speaker SPKR close a listener's ear when such headphone 18A, 18B is engaged with the listener's ear. In some embodiments, CODEC IC 20 may receive the signals from reference microphone R, near-speech microphone NS, and error microphone E of each headphone and perform adaptive noise cancellation for each headphone as described herein. In other embodiments, a CODEC IC or another circuit may be present within headphone assembly 13, communicatively coupled to reference microphone R, near-speech microphone NS, and error microphone E, and configured to perform adaptive noise cancellation as described herein.

Figure 2:
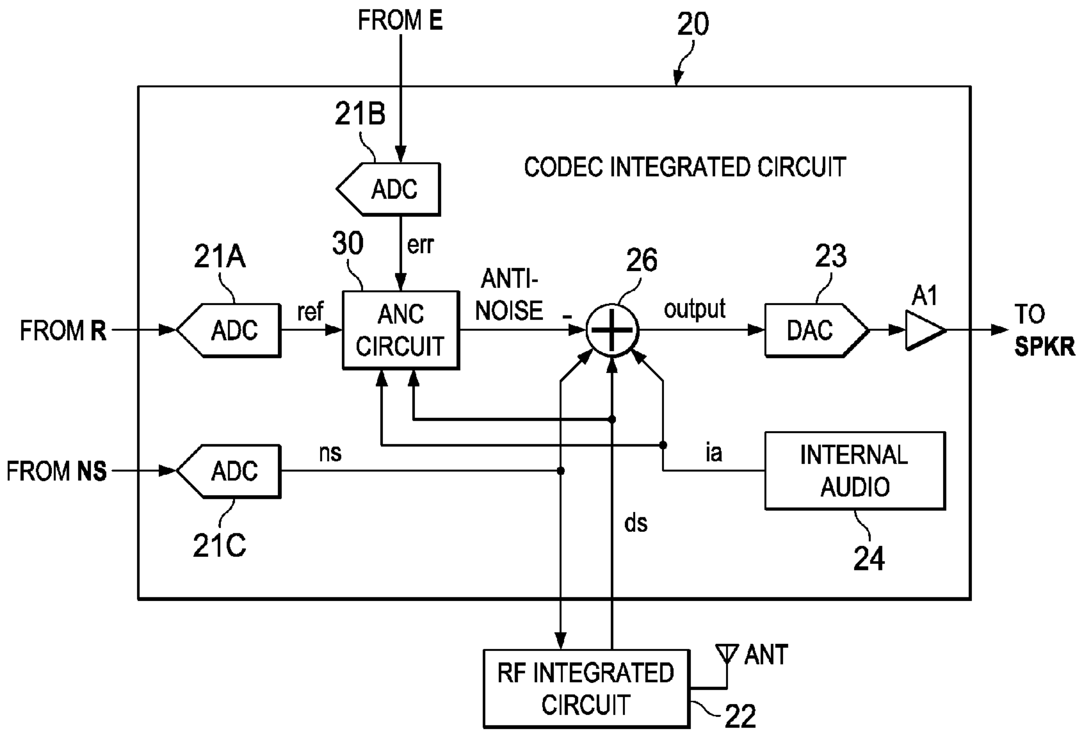
FIG. 2 is a block diagram of selected circuits within the wireless telephone depicted in FIG. 1, in accordance with embodiments of the present disclosure.
Figure 3:
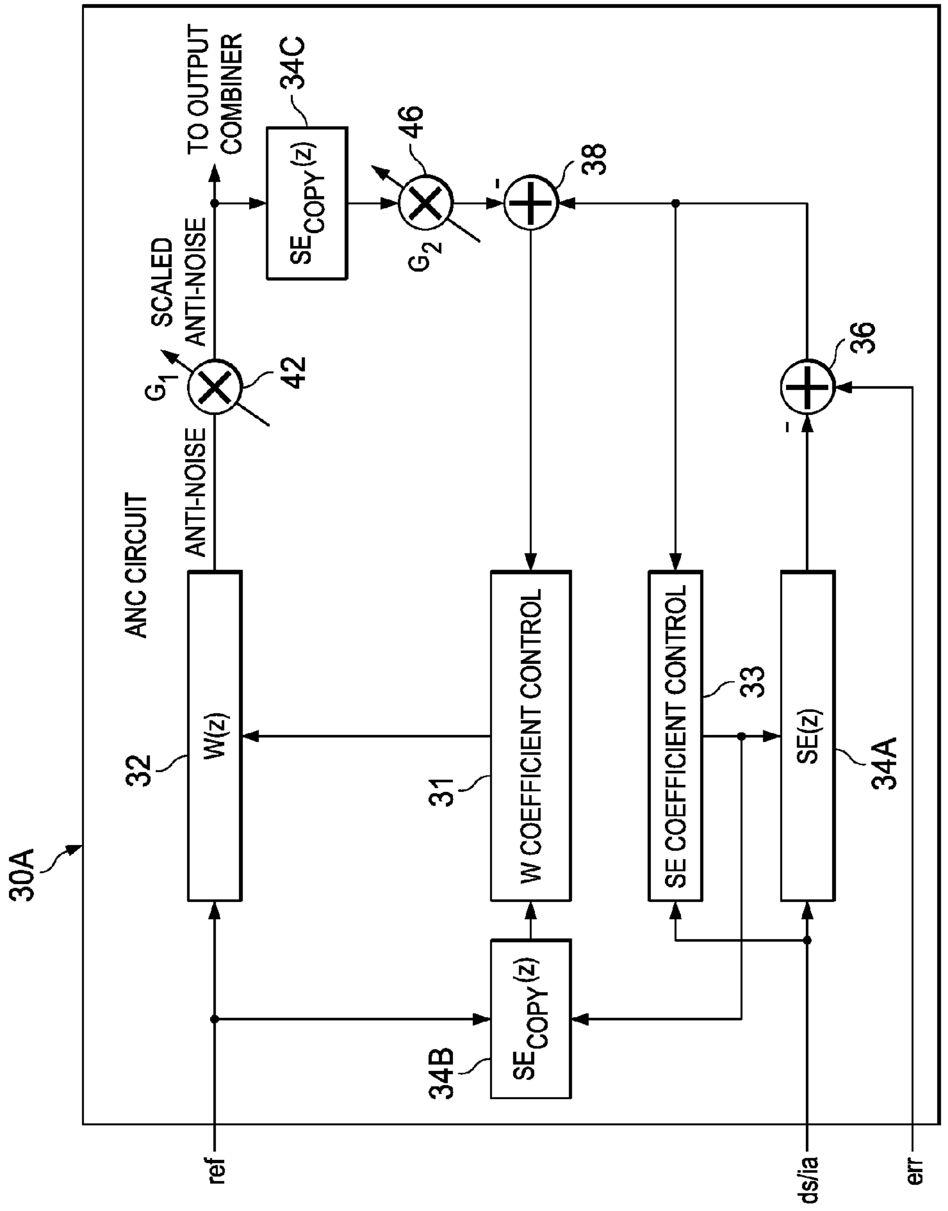
FIG. 3 is a block diagram depicting selected signal processing circuits and functional blocks within an example adaptive noise canceling (ANC) circuit of a coder-decoder (CODEC) integrated circuit of FIG. 2, in accordance with embodiments of the present disclosure.
Figure 4:
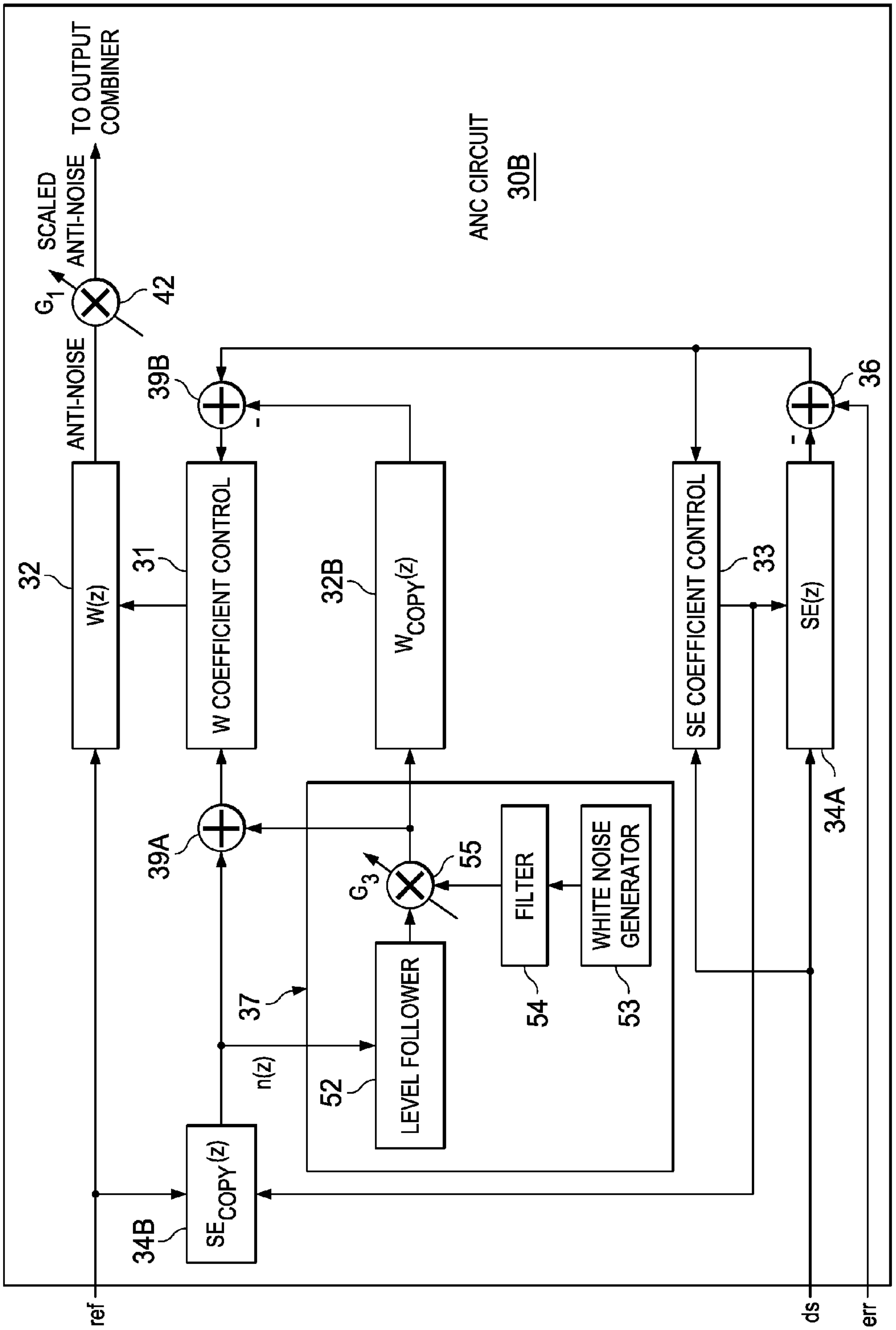
FIG. 4 is a block diagram depicting selected signal processing circuits and functional blocks within another example adaptive noise canceling (ANC) circuit of a coder-decoder (CODEC) integrated circuit of FIG. 2, in accordance with embodiments of the present disclosure.

Referring now to FIG. 2, selected circuits within wireless telephone 10 are shown in a block diagram, which in other embodiments may be placed in whole or in part in other locations such as one or more headphones or earbuds. CODEC IC 20 may include an analog-to-digital converter (ADC) 21A for receiving the reference microphone signal and generating a digital representation ref of the reference microphone signal, an ADC 21B for receiving the error microphone signal and generating a digital representation err of the error microphone signal, and an ADC 21C for receiving the near speech microphone signal and generating a digital representation ns of the near speech microphone signal. CODEC IC 20 may generate an output for driving speaker SPKR from an amplifier A1, which may amplify the output of a digital-to-analog converter (DAC) 23 that receives the output of a combiner 26. Combiner 26 may combine audio signals is from internal audio sources 24, the anti-noise signal generated by ANC circuit 30 (which may be a scaled anti-noise, as shown in FIGS. 3 and 4 below), which by convention has the same polarity as the noise in reference microphone signal ref and is therefore subtracted by combiner 26, and a portion of near speech microphone signal ns so that the user of wireless telephone 10 may hear his or her own voice in proper relation to downlink speech ds, which may be received from radio frequency (RF) integrated circuit 22 and may also be combined by combiner 26. Near speech microphone signal ns may also be provided to RF integrated circuit 22 and may be transmitted as uplink speech to the service provider via antenna ANT.

Referring now to FIG. 3, details of an example ANC circuit 30A are shown in accordance with embodiments of the present disclosure. In some embodiments, ANC circuit 30A may be used to implement ANC circuit 30 of FIG. 2. Adaptive filter 32 may receive reference microphone signal ref and under ideal circumstances, may adapt its transfer function W(z) to be P(z)/S(z) to generate the anti-noise signal, which may be scaled by gain element 42 having a gain $G_1$ (effectively applying a scaling factor to the anti-noise signal equal to gain $G_1$) to generate a scaled anti-noise signal. The scaled anti-noise signal may be provided to an output combiner that combines the scaled anti-noise signal with the audio to be reproduced by the transducer, as exemplified by combiner 26 of FIG. 2. The coefficients of adaptive filter 32 may be controlled by a W coefficient control block 31 that uses a correlation of signals to determine the response of adaptive filter 32, which generally minimizes the error, in a least-mean squares sense, between those components of reference microphone signal ref present in error microphone signal err. The signals compared by W coefficient control block 31 may be the reference microphone signal ref as shaped by a copy of an estimate of the response of path S(z) provided by filter 34B and a modified playback corrected error based at least in part on error microphone signal err. The modified playback corrected error may be generated as described in greater detail below.

By transforming reference microphone signal ref with a copy of the estimate of the response of path S(z), response $SE_{COPY}(z)$, and minimizing the difference between the resultant signal and error microphone signal err, adaptive filter 32 may adapt to the desired response of P(z)/S(z). In addition to error microphone signal err, the signal compared to the output of filter 34B by W coefficient control block 31 may include an inverted amount of downlink audio signal ds and/or internal audio signal ia that has been processed by filter response SE(z), of which response $SE_{COPY}(z)$ is a copy. By injecting an inverted amount of downlink audio signal ds and/or internal audio signal ia, adaptive filter 32 may be prevented from adapting to the relatively large amount of downlink audio and/or internal audio signal present in error microphone signal err. However, by transforming that inverted copy of downlink audio signal ds and/or internal audio signal ia with the estimate of the response of path S(z), the downlink audio and/or internal audio that is removed from error microphone signal err should match the expected version of downlink audio signal ds and/or internal audio signal ia reproduced at error microphone signal err, because the electrical and acoustical path of S(z) is the path taken by downlink audio signal ds and/or internal audio signal ia to arrive at error microphone E. Filter 34B may not be an adaptive filter, per se, but may have an adjustable response that is tuned to match the response of adaptive filter 34A, so that the response of filter 34B tracks the adapting of adaptive filter 34A.

To implement the above, adaptive filter 34A may have coefficients controlled by SE coefficient control block 33, which may compare a source audio signal (e.g., downlink audio signal ds and/or internal audio signal ia) and a playback corrected error, wherein the playback corrected error is equal to error microphone signal err after removal of the source audio signal (as filtered by adaptive filter 34A to represent the expected playback audio delivered to error microphone E) by a combiner 36. SE coefficient control block 33 may correlate the actual source audio signal with the components of the source audio signal that are present in error microphone signal err. Adaptive filter 34A may thereby be adapted to generate a secondary estimate signal from the source audio signal, that when subtracted from error microphone signal err to generate the playback corrected error, includes the content of error microphone signal err that is not due to the source audio signal.

The modified playback corrected error may be communicated to W coefficient control block 31 and compared with the filtered reference microphone signal ref, wherein the modified playback corrected error is equal to the playback corrected error after removal (e.g., by combiner 38) of an unscaled filtered anti-noise signal generated by a biasing portion comprising filter 34C and gain element 46 having a gain $G_2$. Filter 34C may not be an adaptive filter, per se, but may have an adjustable response that is tuned to match the response of adaptive filter 34A, so that the response of filter 34C tracks the adapting of adaptive filter 34A. Filter 34C may apply the response $SE_{COPY}(z)$ (which is a copy of SE(z)) and gain element 46 may apply a multiplicative scaling factor equal to gain $G_2$ to the anti-noise signal generated by filter 32 in order to generate the unscaled filtered anti-noise signal.

As shown in FIG. 3, gain $G_1$ of gain element 42 may be tunable/controllable, thus allowing an ANC effect of ANC circuit 30A as heard by a listener to be controllable. For example, in some embodiments, the scaling factor (e.g., gain $G_1$) applied by gain element 42 may be tunable in response to an ambient audio event (e.g., a siren, alarm, car horn, a person other than the user uttering a phrase, etc., such that an ANC effect is reduced at least momentarily to prevent the ambient audio event from being cancelled to allow the listener to hear the event. As another example, in these and other embodiments, the scaling factor may be controllable by a user of a personal audio device including ANC circuit 30A, such as by user interaction with a user interface of the personal audio device, in response to a voice command uttered by a user of the personal audio device (e.g., "Reduce ANC to 50 percent"). In these and other embodiments, the scaling factor of gain element may be controllable/tunable between values of 0 and 1.

Likewise, also as shown in FIG. 3, gain $G_2$ of gain element 46 may be tunable/controllable, thus counterbalancing for the gain $G_1$ applied by gain element 42, and thus preventing ANC circuit 30A from adapting to any change to gain $G_1$ and undoing any tuning/control of gain $G_1$. Thus, in some embodiments, gain $G_2$ of gain element 46 may be responsive to and a function of gain $G_1$ applied by gain element 42. For example, in some of such embodiments, gain $G_2$ may be approximately equal (e.g., within any relevant engineering or programming tolerances) to one minus the inverse of gain $G_1$ (e.g., $G_2=1-1/G_1$).

Referring now to FIG. 4, details of another example ANC circuit 30B are shown in accordance with embodiments of the present disclosure. In some embodiments, ANC circuit 30B may be used to implement ANC circuit 30 of FIG. 2. ANC circuit 30B may be similar in many respects to ANC circuit 30A of FIG. 3, so only the differences from ANC circuit 30A may be described below. As in ANC circuit 30A, ANC circuit 30B includes gain element 42 which may scale the anti-noise signal generated by adaptive filter 32 by a gain $G_1$ to generate the scaled anti-noise signal (effectively applying a scaling factor to the anti-noise signal equal to gain $G_1$). The scaled anti-noise signal may be provided to an output combiner that combines the scaled anti-noise signal with the audio to be reproduced by the transducer, as exemplified by combiner 26 of FIG. 2. However, ANC circuit 30B does not have a biasing portion comprising filter 34C and gain element 46 as in ANC circuit 30A, but instead includes a biasing portion including a noise source 37 for generating an injected noise signal n(z) and a filter 32B that may apply the response $W_{COPY}(z)$ (which is a copy of W(z)) to the injected noise signal to generate a filtered injected noise signal. Filter 32B may not be an adaptive filter, per se, but may have an adjustable response that is tuned to match the response of adaptive filter 32, so that the response of filter 34B tracks the adapting of adaptive filter 32. A combiner 39A may add injected noise signal n(z) to the output of adaptive filter 34B that is provided to W coefficient control block 31. In addition, noise signal n(z), as shaped by filter 32B, may be subtracted from the playback corrected error output by combiner 36 by a combiner 39B so that injected noise signal n(z) is asymmetrically added to the correlation inputs to W coefficient control block 31, with the result that the response W(z) of adaptive filter 32 is biased by the correlated injection of noise signal n(z) to each correlation input to W coefficient control block 31. Because the injected noise signal appears directly at the reference input to W coefficient control block 31, does not appear in error microphone signal err, and only appears at the other input to W coefficient control block 31 via the combining of the filtered noise at the output of filter 32B by combiner 39B, W coefficient control block 31 will adapt W(z) to attenuate the frequencies present in noise(z). Thus, content of injected noise signal n(z) may not appear in the anti-noise signal, only in the response W(z) of adaptive filter 32 which will have amplitude decreases at the frequencies/bands in which injected noise signal n(z) has energy.

As shown in FIG. 4, noise source 37 may include a white noise generator 53 to provide a biasing noise source which may be shaped by a filter 54 (which may include one or more biquad filters, as is known in the art), the output of which may be input to a gain element 55 having a gain $G_3$ (effectively applying a scaling factor to the output of filter 54 equal to gain $G_3$). A gain of gain element 55 may also be scaled by some level of the ambient noise present in reference microphone signal ref via a level follower 52, such that the injected noise signal n(z) may be at a magnitude below that of ambient noise, such that injected noise signal n(z) is substantially inaudible to the listener.

As shown in FIG. 4, gain $G_1$ of gain element 42 may be tunable/controllable, thus allowing an ANC effect of ANC circuit 30B as heard by a listener to be controllable. For example, in some embodiments, the scaling factor (e.g., gain $G_1$) applied by gain element 42 may be tunable in response to an ambient audio event (e.g., a siren, alarm, car horn, a person other than the user uttering a phrase, etc.), such that an ANC effect is reduced at least momentarily to prevent the ambient audio event from being cancelled to allow the listener to hear the event. As another example, in these and other embodiments, the scaling factor may be controllable by a user of a personal audio device including ANC circuit 30B, such as by user interaction with a user interface of the personal audio device, in response to a voice command uttered by a user of the personal audio device (e.g., "Reduce ANC to 50 percent"). In these and other embodiments, the scaling factor of gain element may be controllable/tunable between values of 0 and 1.

Likewise, also as shown in FIG. 4, gain $G_3$ of gain element 55 may be tunable/controllable so as to control injected noise signal n(z), thus counterbalancing for the gain $G_1$ applied by gain element 42, and thus preventing ANC circuit 30A from adapting to any change to gain $G_1$ and undoing any tuning/control of gain $G_1$. Thus, in some embodiments, gain $G_2$ of gain element 46 may be responsive to and a function of gain $G_1$ applied by gain element 42. For example, in some of such embodiments, gain $G_3$ may be approximately inversely proportional (e.g., within any relevant engineering or programming tolerances) to gain $G_1$ (e.g., $G_3=1/G_1$).

As used herein, when two or more elements are referred to as "coupled" to one another, such term indicates that such two or more elements are in electronic communication whether connected indirectly or directly, with or without intervening elements.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, or component, whether or not it or that particular function is activated, turned on, or unlocked, as long as that apparatus, system, or component is so adapted, arranged, capable, configured, enabled, operable, or operative.

All examples and conditional language recited herein are intended for pedagogical objects to aid the reader in understanding the disclosure and the concepts contributed by the inventor to furthering the art, and are construed as being without limitation to such specifically recited examples and conditions. Although embodiments of the present disclosures have been described in detail, it should be understood that various changes, substitutions, and alterations could be made hereto without departing from the spirit and scope of the disclosure.

What is claimed is:

1. An integrated circuit for implementing at least a portion of a personal audio device, comprising:

an output for providing a signal to a transducer including both a source audio signal for playback to a listener and a scaled anti-noise signal for countering the effect of ambient audio sounds in an acoustic output of the transducer;

a reference microphone input for receiving a reference microphone signal indicative of the ambient audio sounds;

an error microphone input for receiving an error microphone signal indicative of the output of the transducer and the ambient audio sounds at the transducer; and a processing circuit comprising:

an adaptive filter having a response that generates an unscaled anti-noise signal from the reference microphone signal to reduce the presence of the ambient audio sounds heard by the listener;

a scaling portion that generates the scaled anti-noise signal by applying a scaling factor to the anti-noise signal;

a coefficient control block that shapes the response of the adaptive filter in conformity with the reference microphone signal and the error microphone signal by adapting the response of the adaptive filter to minimize the ambient audio sounds at the error microphone signal; and a biasing portion configured to further adjust the response of the adaptive filter independent of the source audio signal by altering an input to the coefficient control block of the adaptive filter to compensate for the scaling factor.

2. The integrated circuit of claim 1, wherein:

the processing circuit further comprises a secondary path estimate filter configured to model an electro-acoustic path of the source audio signal;

the biasing portion generates an unscaled filtered anti-noise signal by applying a second scaling factor to the response of the secondary path estimate filter to the scaled anti-noise signal; and the coefficient control block shapes the response of the adaptive filter in conformity with the reference microphone signal and a modified playback corrected error signal by adapting the response of the adaptive filter to minimize the ambient audio sounds in the error microphone signal, wherein the playback corrected error is based on a difference between the error microphone signal and the source audio signal and the modified playback corrected error signal is based on a difference between the playback corrected error signal and the unscaled filtered anti-noise signal.

3. The integrated circuit of claim 2, wherein the second scaling factor defines a gain, wherein the gain is the ratio of a filtered anti-noise signal generated by the secondary path estimate filter to the unscaled filtered anti-noise generated by the second scaling portion.

4. The integrated circuit of claim 2, wherein the second scaling factor is a function of the scaling factor.

5. The integrated circuit of claim 4, wherein the second scaling factor is approximately equal to one minus the inverse of the scaling factor.

6. The integrated circuit of claim 1, wherein the biasing portion generates an injected noise that is combined with an input to the coefficient control block so that the response of the adaptive filter is biased by the coefficient control block adapting to attenuate the injected noise.

7. The integrated circuit of claim 6, wherein the biasing portion further comprises a copy of the adaptive filter to receive the injected noise and the output of the copy of the adaptive filter is removed from the error microphone signal.

8. The integrated circuit of claim 6, wherein the processing circuit further comprises a secondary path adaptive filter having a secondary path response that shapes the source audio signal and a combiner that removes the shaped source audio signal from the error microphone signal to provide a playback corrected error signal indicative of the generated anti-noise delivered to the listener and the ambient audio sounds, and wherein the processing circuit shapes the response of the adaptive filter in conformity with the playback corrected error signal and the reference microphone signal.

9. The integrated circuit of claim 6, wherein the biasing portion applies a second scaling factor to the injected noise to control the injected noise.

10. The integrated circuit of claim 9, wherein the second scaling factor is a function of the scaling factor.

11. The integrated circuit of claim 10, wherein the second scaling factor is approximately inversely proportional to the scaling factor.

12. The integrated circuit of claim 1, wherein the scaling factor has a value between 0 and 1.

13. The integrated circuit of claim 1, wherein the scaling factor defines a gain, wherein the gain is the ratio of the anti-noise signal generated by the adaptive filter to the scaled anti-noise generated by the scaling portion.

14. The integrated circuit of claim 1, wherein the scaling factor is tunable in response to an ambient audio event.

15. The integrated circuit of claim 1, wherein the scaling factor is controllable by a user of the personal audio device.

16. The integrated circuit of claim 15, wherein the scaling factor is controllable in response to user interaction with a user interface of the personal audio device.

17. The integrated circuit of claim 15, wherein the scaling factor is controllable in response to a voice command uttered by a user of the personal audio device.

18. A method comprising:

receiving a reference microphone signal indicative of ambient audio sounds;

receiving an error microphone signal indicative of an output of a transducer and the ambient audio sounds at the transducer;

generating a source audio signal for playback to a listener;

adaptively generating an anti-noise signal for countering the effects of ambient audio sounds at an acoustic output of the transducer by adapting a response of an adaptive filter that filters the reference microphone signal in conformity with the error microphone signal and the reference microphone signal to minimize the ambient audio sounds in the error microphone;

generating a scaled anti-noise signal by applying a scaling factor to the anti-noise signal;

further adjusting the response of the adaptive filter independent of the source audio signal by altering an input to a coefficient control block of the adaptive filter to compensate for the scaling factor; and combining the scaled anti-noise signal with the source audio signal to generate an audio signal provided to the transducer.

19. The method of claim 18, further comprising:

generating an unscaled filtered anti-noise signal by applying a second scaling factor to a response of a secondary path estimate filter to the scaled anti-noise signal, wherein the secondary path estimate filter configured models an electro-acoustic path of the source audio signal; and shaping the response of the adaptive filter in conformity with the reference microphone signal and a modified playback corrected error signal by adapting the response of the adaptive filter to minimize the ambient audio sounds in the error microphone signal, wherein the playback corrected error is based on a difference between the error microphone signal and the source audio signal and the modified playback corrected error signal is based on a difference between the playback corrected error signal and an unscaled filtered anti-noise signal.

20. The method of claim 19, wherein the second scaling factor defines a gain, wherein the gain is the ratio of a filtered anti-noise signal generated by the secondary path estimate filter to the unscaled filtered anti-noise generated by the second scaling portion.

21. The method of claim 19, wherein the second scaling factor is a function of the scaling factor.

22. The method of claim 21, wherein the second scaling factor is approximately equal to one minus the inverse of the scaling factor.

23. The method of claim 18, further comprising generating an injected noise that is combined with an input to the coefficient control block so that the response of the adaptive filter is biased by the coefficient control block adapting to attenuate the injected noise.

24. The method of claim 23, further comprising:

receiving the injected noise by a copy of the adaptive filter; and removing an output of the copy of the adaptive filter from the error microphone signal.

25. The method of claim 23, further comprising:

shaping the source audio signal with a secondary path adaptive filter having a secondary path response;

removing the shaped source audio signal from the error microphone signal to provide a playback corrected error signal indicative of the generated anti-noise delivered to the listener and the ambient audio sounds; and shaping the response of the adaptive filter in conformity with the playback corrected error signal and the reference microphone signal.

26. The method of claim 23, further comprising applying a second scaling factor to the injected noise to control the injected noise.

27. The method of claim 26, wherein the second scaling factor is a function of the scaling factor.

28. The method of claim 27, wherein the second scaling factor is approximately inversely proportional to the scaling factor.

29. The method of claim 18, wherein the scaling factor has a value between 0 and 1.

30. The method of claim 18, wherein the scaling factor defines a gain, wherein the gain is the ratio of the anti-noise signal generated by the adaptive filter to the scaled anti-noise generated by the scaling portion.

31. The method of claim 18, wherein the scaling factor is tunable in response to an ambient audio event.

32. The method of claim 18, wherein the scaling factor is controllable by a user of a personal audio device comprising or communicatively coupled to the transducer.

33. The method of claim 32, wherein the scaling factor is controllable in response to user interaction with a user interface of the personal audio device.

34. The method of claim 32, wherein the scaling factor is controllable in response to a voice command uttered by a user of the personal audio device.

* * * * *